(12) United States Patent
Zaiki

(10) Patent No.: US 9,968,320 B2
(45) Date of Patent: May 15, 2018

(54) X-RAY DIAGNOSTIC APPARATUS

(71) Applicant: Toshiba Medical Systems Corporation, Otawara-shi (JP)

(72) Inventor: Ryuji Zaiki, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 290 days.

(21) Appl. No.: 14/823,550

(22) Filed: Aug. 11, 2015

(65) Prior Publication Data

US 2015/0342548 A1 Dec. 3, 2015

Related U.S. Application Data

(63) Continuation of application No. PCT/JP2014/053532, filed on Feb. 14, 2014.

(30) Foreign Application Priority Data

Feb. 14, 2013 (JP) .................................. 2013-026637
Feb. 14, 2014 (JP) .................................. 2014-026604

(51) Int. Cl.
  *A61B 6/00* (2006.01)
  *A61B 6/02* (2006.01)
  *A61B 6/08* (2006.01)

(52) U.S. Cl.
  CPC .............. *A61B 6/467* (2013.01); *A61B 6/022* (2013.01); *A61B 6/08* (2013.01); *A61B 6/4441* (2013.01);
  (Continued)

(58) Field of Classification Search
  None
  See application file for complete search history.

(56) References Cited

U.S. PATENT DOCUMENTS

2008/0253519 A1 10/2008 Bonfiglio et al.
2012/0249534 A1* 10/2012 Kanagawa ......... H04N 13/0022
                                                            345/419

(Continued)

FOREIGN PATENT DOCUMENTS

JP          09-084000 A      3/1997
JP          2008-529707 A    8/2008
(Continued)

OTHER PUBLICATIONS

International Search Report dated Mar. 18, 2014 for PCT/JP2014/053532 filed Feb. 14, 2014 with English Translation.

(Continued)

*Primary Examiner* — Hoon Song
(74) *Attorney, Agent, or Firm* — Oblon, McClelland, Maier & Neustadt, L.L.P.

(57) ABSTRACT

According to one embodiment, an X-ray diagnostic apparatus includes an X-ray tube that generates X-rays, an X-ray detector that detects X-rays generated from the X-ray tube and transmitted through an object, a supporting mechanism supports the X-ray tube and the X-ray detector in directions to face each other, a display displays an X-ray image concerning the object based on an output from the X-ray detector, position specifying circuitry specifies a position of the face of a user who is visually recognizing the display, and moving circuitry moves the supporting mechanism to an imaging position corresponding to the specified position of the face of the user.

10 Claims, 8 Drawing Sheets

(52) U.S. Cl.
CPC ............... *A61B 6/46* (2013.01); *A61B 6/461* (2013.01); *A61B 6/545* (2013.01)

(56) References Cited

U.S. PATENT DOCUMENTS

| | | | | |
|---|---|---|---|---|
| 2013/0089183 A1* | 4/2013 | Sura | ..................... | A61B 6/4225 378/98.2 |
| 2014/0198897 A1* | 7/2014 | Sakaguchi | ............. | A61B 6/022 378/37 |
| 2014/0205061 A1* | 7/2014 | Sakaguchi | ............. | A61B 6/486 378/41 |

FOREIGN PATENT DOCUMENTS

| | | |
|---|---|---|
| JP | 2009-072360 A | 4/2009 |
| JP | 2011-181991 A | 9/2011 |
| JP | 2011-259373 A | 12/2011 |
| JP | 2012-080294 A | 4/2012 |
| JP | 2012-223363 A | 11/2012 |
| JP | 2014-028123 A | 2/2014 |

OTHER PUBLICATIONS

International Written Opinion dated Mar. 18, 2014 for PCT/JP2014/053532 filed Feb. 14, 2014.

* cited by examiner

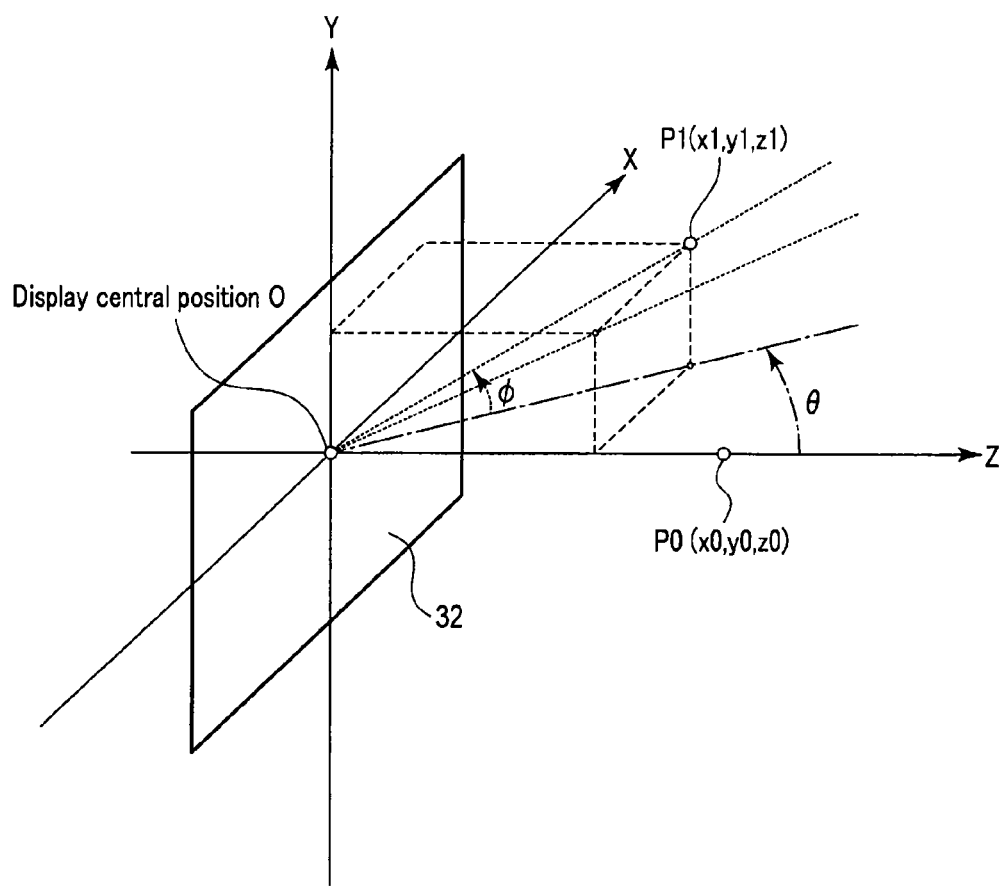
F I G. 3

X-RAY DIAGNOSTIC APPARATUS

CROSS-REFERENCE TO RELATED APPLICATIONS

This application is a Continuation Application of PCT. Application No. PCT/JP2014/053532, filed Feb. 14, 2014 and based upon and claims the benefit of priority from the Japanese Patent Application No. 2013-026637, filed Feb. 14, 2013, and No. 2014-026604, filed Feb. 14, 2014, the entire contents of all of which are incorporated herein by reference.

FIELD

Embodiments described herein relate generally to an X-ray diagnostic apparatus.

BACKGROUND

There is available a stereoscopic vision technique of allowing stereoscopic viewing of an image by displaying a left-eye image and a right-eye image having an angular difference on a monitor. Stereoscopic vision allows the user to easily grasp the forward/backward relationship between objects and the unevenness information of an object surface, which are difficult to know on a general two-dimensional display. Recently, the stereoscopic vision technique has been applied to the medical field. For example, the user can precisely grasp the positional relationship between neighboring organs, blood vessels, and the like of an object by acquiring a left-eye image and a right-eye image for stereoscopic vision of the object from a specific direction and interpreting a stereoscopic video of the object. Therefore, the stereoscopic vision technique makes it possible to perform safer and more accurate surgical operations and the like. However, the user sometimes wants to stereoscopically view the object from another direction. At this time, the user needs to re-set an imaging angle by, for example, inputting a desired stereoscopic viewing direction. However, for example, during a surgical operation, it is cumbersome for the user to perform the above setting operation for an imaging angle. Acquiring a plurality of images in advance to cope with stereoscopic vision of an object from a plurality of directions can facilitate interpretation of a stereoscopic vision video from another direction with respect to the object. However, acquiring a plurality of images by using an X-ray imaging apparatus or the like will increase the exposure dose of an object.

BRIEF DESCRIPTION OF THE DRAWINGS

FIG. 3 is a view for explaining user movement displacement.

DETAILED DESCRIPTION

Figure 1:
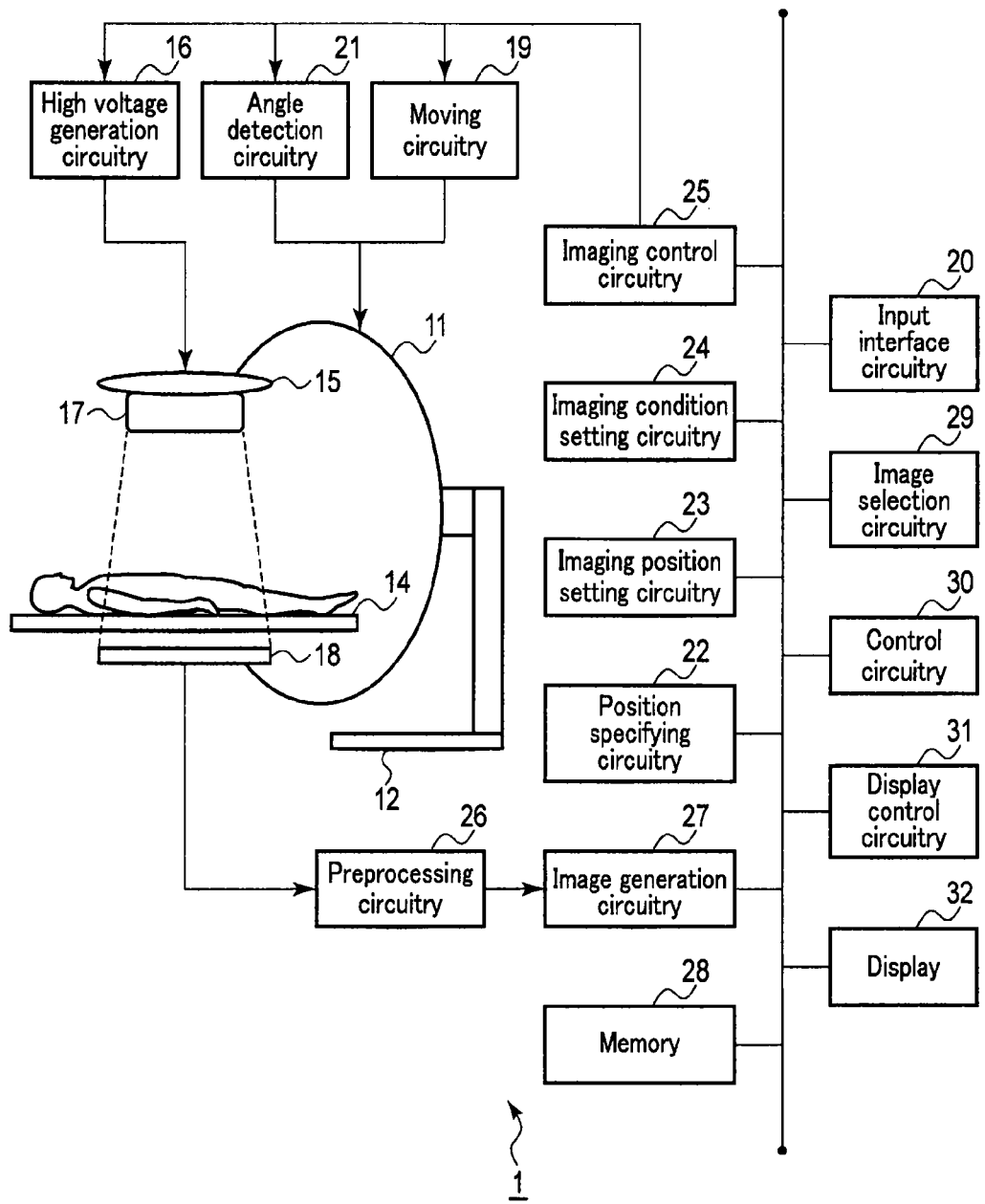
FIG. 1 is a block diagram showing an example of the arrangement of an X-ray diagnostic apparatus according to this embodiment.

According to one embodiment, an X-ray diagnostic apparatus includes an X-ray tube that generates X-rays, an X-ray detector that detects X-rays generated from the X-ray tube and transmitted through an object, a supporting mechanism supports the X-ray tube and the X-ray detector in directions to face each other, a display displays an X-ray image concerning the object based on an output from the X-ray detector, position specifying circuitry specifies a position of the face of a user who is visually recognizing the display, and moving circuitry moves the supporting mechanism to an imaging position corresponding to the specified position of the face of the user.

An X-ray diagnostic apparatus 1 according to this embodiment will be described below with reference to the accompanying drawings. Note that the same reference numerals in the following description denote constituent elements having almost the same functions and arrangements, and a repetitive description will be made only when required.

FIG. 1 is a block diagram showing an example of the arrangement of the X-ray diagnostic apparatus 1 according to this embodiment. As shown in FIG. 1, the X-ray diagnostic apparatus 1 includes a supporting mechanism (a C-arm 11 and a C-arm support mechanism 12), a bed 13, a top 14, an X-ray generator 15, high voltage generation circuitry 16, an X-ray stop 17, an X-ray detector 18, moving circuitry 19, input interface circuitry 20, angle detection circuitry 21, a position specifying circuitry 22, an imaging position setting circuitry 23, an imaging condition setting circuitry 24, an imaging control circuitry 25, preprocessing circuitry 26, image generation circuitry 27, a memory 28, image selection circuitry 29, control circuitry 30, display control circuitry 31, and a display 32.

The gantry of the X-ray diagnostic apparatus 1 includes the C-arm 11, the C-arm support mechanism 12, the bed 13, and the top 14.

The supporting mechanism includes the C-arm 11 and the C-arm support mechanism 12. The C-arm support mechanism 12 rotatably supports the C-arm 11. The C-arm 11 holds the X-ray generator 15 on its one end. The X-ray generator 15 is a vacuum tube which generates X-rays. The X-ray generator 15 generates X-rays upon reception of a high voltage (tube voltage) from the high voltage generation circuitry 16. The X-ray generator 15 has a radiation window for radiating X-rays. The X-ray stop 17 is attached to the radiation window of the X-ray generator 15. The X-ray stop 17 is a beam cone limiter which can adjust an X-ray irradiation field on the detection surface of the X-ray detector 18. Adjusting an X-ray irradiation field by using the X-ray stop 17 can reduce unnecessary radiation exposure on an object. The C-arm 11 holds the X-ray detector 18 on the other end so as to make it face the X-ray generator 15. The X-ray detector 18 includes a plurality of X-ray detection elements. The plurality of X-ray detection elements are arranged in a two-dimensional array. A detector in a two-dimensional array is called an FPD (Flat Panel Display). Each element of the FPD detects the X-rays emitted from the X-ray generator 15 and transmitted through the object. Each element of the FPD outputs an electrical signal corresponding to a detected X-ray intensity. A line connecting the focus of the radiation window of the X-ray generator 15 and the central position of the X-ray detection surface of the X-ray detector 18 is called an imaging axis (the fifth rotation axis). The rotation of the X-ray detector 18 around the fifth rotation axis determines the top and bottom of an obtained image. Note that the top, bottom, left, and right of an image can be changed as needed by changing a method of reading out an electrical signal from each element of the X-ray detector 18.

Figure 2:
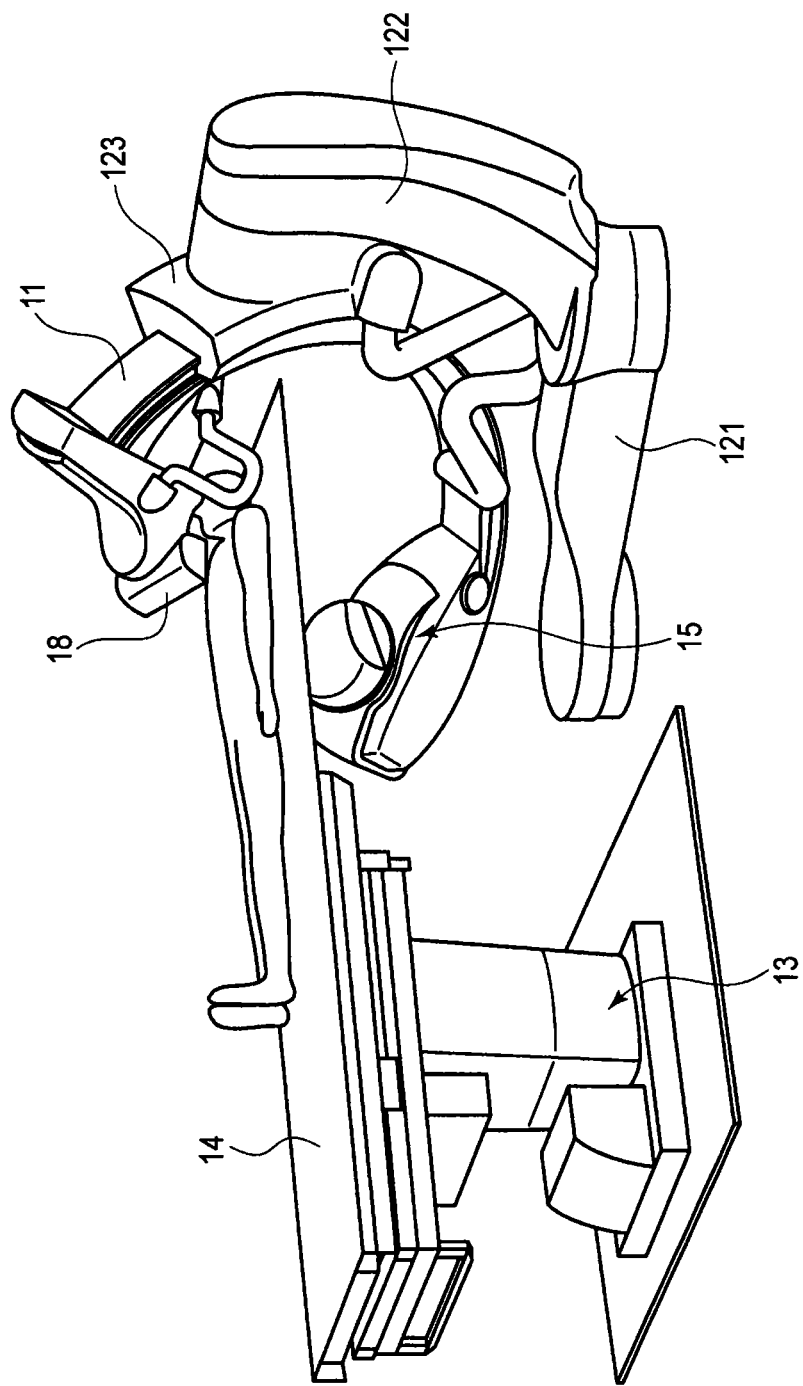
FIG. 2 is a perspective view showing an outer appearance of the gantry of the X-ray diagnostic apparatus according to this embodiment.

FIG. 2 is a perspective view showing an outer appearance of the gantry of the X-ray diagnostic apparatus 1 according to this embodiment. Note that the C-arm support mechanism 12 may be of either a ceiling suspension type that holds the C-arm 11 while suspending it from the ceiling or a floor mount type that holds the C-arm 11 mounted on the floor. This embodiment will exemplify the floor mount type. The C-arm support mechanism 12 includes a floor swivel arm 121, a stand 122, and an arm holder 123. The floor swivel arm 121 is provided, at its one end, on the floor surface so as to freely swivel around the first rotation axis. The stand 122 is supported on the other end of the floor swivel arm 121 so as to be rotatable about the second rotation axis. The first and second rotation axes are almost parallel to the orthogonal axis. The arm holder 123 is supported on the stand 122 so as to be rotatable around the third rotation axis. The third rotation axis is an axis almost orthogonal to the orthogonal axis. The C-arm 11 is supported on the arm holder 123 so as to freely rotate (slide) in an arc along the shape of the C-arm 11. The rotation axis of this sliding rotation is called the fourth rotation axis. Note that the C-arm support mechanism 12 may hold the C-arm 11 so as to allow it to move in the long- and short-axis directions (to be described later).

Note that in this embodiment, it is described that the C-arm 11 holds the X-ray generator 15 and the X-ray detector 18, and the C-arm support mechanism 12 rotatably holds the C-arm 11. However, other support mechanisms may be used as long as they can hold the X-ray generator 15 and the X-ray detector 18 so as to make them face each other. For example, the C-arm 11 and the C-arm support mechanism 12 can be replaced with a first holding unit which rotatably holds the X-ray generator 15 and a second holding unit which rotatably holds the X-ray detector 18. In this case, for example, the first holding unit has a mechanism mounted on the floor. The second holding unit has a mechanism suspended from the ceiling. The first and second holding units hold the X-ray generator 15 and the X-ray detector 18 in directions in which they face each other. It is possible to perform continuous X-ray imaging by, for example, controlling the first and second holding units so as to synchronize their rotating operations.

The bed 13 and the top 14 are arranged between the X-ray generator 15 and the X-ray detector 18. The bed 13 supports the top 14, on which an object is placed, so as to make the top 14 movable in three orthogonal axes. Assume that the three orthogonal axes are defined by the short axis of the top 14, the long axis of the top 14, and an orthogonal axis orthogonal to the short- and long-axes. A direction along the long axis of the top 14 will be referred to as a long-axis direction. In addition, a direction along the short axis of the top 14 will be referred to as a short-axis direction. In addition, a direction along the orthogonal axis will be referred to as an orthogonal-axis direction.

The moving circuitry 19 independently rotates the C-arm 11 and the C-arm support mechanism 12 (a combination of which is referred to as the supporting mechanism) in the first to fifth rotation axes under the control of the imaging control circuitry 25 (to be described later). In addition, the moving circuitry 19 makes the top 14 slide in the long-axis direction or the short-axis direction and makes it move up and down in the orthogonal-axis direction under the control of the imaging control circuitry 25 (to be described later). In addition, the moving circuitry 19 rotates and moves the top 14 so as to tilt it with respect to the mounting surface of the bed 13 by using, as a rotation axis, an axis parallel to at least one of the long-axis direction and the short-axis direction. In the following description, sliding movement, up/down movement, and rotation/movement concerning the movement of the C-arm 11 and the C-arm support mechanism 12 will be collectively referred to as movement.

The input interface circuitry 20 includes, for example, a predetermined processor and a memory. The input interface circuitry 20 functions as an interface for inputting instruction information issued by the user to the X-ray diagnostic apparatus 1. As the input interface circuitry 20, an input device such as a mouse, keyboard, trackball, touch panel, or buttons can be used as needed. Instruction information includes a move instruction for the C-arm 11, a start instruction for X-ray imaging, a start instruction for imaging angle setting processing, a set instruction for an imaging condition, and a set instruction for a reference visual line.

The input interface circuitry 20 includes an operation console for moving the C-arm 11 and the C-arm support mechanism 12. The operation console includes, for example, buttons, a handle, and a trackball which are used to rotate the C-arm 11 about the above rotation axes independently. The user can move the C-arm 11 and the C-arm support mechanism 12 to desired positions by operating the operation console.

The input interface circuitry 20 includes a switch (to be referred to as an imaging switch hereinafter) for triggering the start of X-ray imaging by the X-ray diagnostic apparatus 1. The imaging switch is typically a foot switch. The imaging control circuitry 25 (to be described later) controls each unit for starting X-ray imaging in response to the pressing of the imaging switch.

The input interface circuitry 20 includes a switch (to be referred to as a setting switch hereinafter) for triggering the start of imaging angle setting processing (to be described later) by the X-ray diagnostic apparatus 1. The imaging control circuitry 25 (to be described later) executes imaging angle setting processing (to be described later) by the X-ray diagnostic apparatus 1 in response to the pressing of the setting switch. Note that the setting switch may also function as an imaging switch (to be referred to as a common switch hereinafter). In response to the pressing of the common switch, the imaging control circuitry 25 executes imaging angle setting processing (to be described later) and then automatically controls each unit to start X-ray imaging.

X-ray imaging conditions include, for example, conditions such as a tube current value, a tube voltage value, and an imaging time. Imaging conditions are input in accordance with user operations on the imaging condition setting support screen displayed on the display 32 (to be described later). The imaging condition setting support screen has entry fields displayed to allow the user to enter a plurality of parameters respectively corresponding to the above conditions.

A visual line is defined by a stereoscopic target position, a visual line direction, and a display direction. A stereoscopic target position is information for determining the central position of an object which the user wants to stereoscopically see. When implementing stereoscopic vision by the intersection technique, a stereoscopic target position overlaps the position of a convergence point at which the right- and left-eye visual lines intersect with each other. A visual line direction is information for determining a direction in which a stereoscopic target position is seen. A display direction is information for determining the top, bottom, left, and right of an object when a stereoscopic target position is seen from a visual line direction. When a stereoscopic vision video corresponding to the visual line of an object set by the user is recognized, the video is a stereoscopic vision video of the object when the stereoscopic target position is seen from the visual line direction. The central position of this video corresponds to the stereoscopic target position. The top, bottom, left, and right of the stereoscopic vision video respectively correspond to the top, bottom, left, and right defined by the display direction.

A reference visual line indicates a reference for a visual line in a series of medical treatment or the like concerning an object. For example, a reference visual line is preferably defined by the position of an object as the most desirable gaze point, a direction in which the position is seen, and the top, bottom, left, and right of the image. For example, a reference visual line is input in accordance with a user operation on the visual line setting image displayed on the display 32 (to be described later). The visual line setting image is a 3D image concerning an object which is reconstructed based on a plurality of X-ray image data obtained by the X-ray diagnostic apparatus 1. The user can input a stereoscopic target position, a visual line direction, and a display direction by operating the 3D image displayed on the display 32 by using a mouse or the like of the input interface circuitry 20. More specifically, the user can input a stereoscopic target position by performing a specific operation, e.g., clicking with the mouse, on the visual line setting image. The user can also input a visual line direction and a display direction by rotating and moving the visual line setting image with the mouse. A visual line direction corresponds to a direction in which the displayed visual line setting image is seen. In addition, a display direction (the top, bottom, left, and right of the stereoscopic vision video) corresponds to the top, bottom, left, and right of the displayed visual line setting image. A visual line setting image is a 3D image concerning the object acquired by the X-ray diagnostic apparatus 1. The X-ray diagnostic apparatus 1 can therefore set an imaging position for the patient placed on the top 14 in accordance with the stereoscopic target position, the visual line direction, and the display direction which are set on the visual line setting image. This allows the user to set a reference visual line. Note that a visual line setting image is not limited to the above image as long as the coordinate system of the visual line setting image and a coordinate system concerning imaging are made to correspond to a top coordinate system having a predetermined position on the top 14 as an origin or the coordinate system of the C-arm 11.

For example, a visual line setting image may be a plurality of 2D images of an object which are obtained by the X-ray diagnostic apparatus 1. In this case, for example, the user designates a stereoscopic target position on the first plane of a 2D image of the object concerning the first plane. The user then designates a stereoscopic target position on the second plane of a 2D image of the object concerning the second plane different from the first plane. A stereoscopic target position is then decided by user operations on the two 2D images concerning the different planes. A visual line direction and a display direction are decided by user operations (e.g., rotating an image) on a 2D image of the object corresponding to the first plane or a 2D image of the object corresponding to the second plane. With the above operations, the user can set a reference visual line.

In addition, if patient information such as the posture, body shape, age, and sex of the patient is known, it is possible to specify a region of the patient placed on the top 14 in a top coordinate system having a predetermined position on the top 14 as an origin. For this reason, a visual line setting image may be a human body model image imitating a human body.

In addition, a 3D image of a visual line setting image may be an image reconstructed based on the volume data acquired by another modality, e.g., an X-ray CT (Computed Tomography) apparatus.

In addition, a reference visual line may be set in accordance with the position of the C-arm 11 moved to the reference visual line and the position of the C-arm support mechanism 12. More specifically, the user moves the fifth rotation axis to the position of the reference visual line by operating the input interface circuitry 20. The user can then set a reference visual line by pressing a button or the like for setting a reference visual line.

The angle detection circuitry 21 includes, for example, a predetermined processor and a memory. The angle detection circuitry 21 detects five rotational angles respectively corresponding to the first to fifth rotation axes. The angle detection circuitry 21 detects five rotational angles in response to pressing of a button of the input interface circuitry 20 which is used to set a reference visual line. A reference visual line is set based on the detected five rotational angles.

The position specifying circuitry 22 includes, for example, a predetermined processor and a memory. The position specifying circuitry 22 specifies a user movement displacement and a reference user parallax.

A user movement displacement is a parameter indicating how much and in which direction the face of the user has moved from a reference position. A reference position is, for example, the position of the face when the user stands at a position to mainly browse the display 32. The position to mainly browse the display 32 corresponds to, for example, a position where the user actually performs a procedure on an object. The position specifying circuitry 22 specifies the position of the face of the user (to be simply referred to as the user position hereinafter). The user position represents the position of a feature point on the face of the user, for example, the midpoint of a straight line connecting the pupil position of the right eye and the pupil position of the left eye of the user. The position specifying circuitry 22 specifies the user position by detecting a feature portion such as the eye, nose, or mouth with respect to an image of the user imaged by a camera or the like. A device such as a camera may be an external device. In this case, the position specifying circuitry 22 receives an image concerning the user input from the external device. The position specifying circuitry 22 sets a reference user position in response to the pressing of a button of the input interface circuitry 20 which is used to set a reference user position. Note that the position specifying circuitry 22 may set a reference user position in response to a specific gesture motion by the user. A gesture motion can be detected by a device such as a camera. A gesture motion is preferably a motion which can be easily performed, for example, "raising the hand" or "shaking the head", by even the user who is performing a procedure. The reference user position can be changed as needed before or during a procedure by a gesture motion and an operation on the input interface circuitry 20. For example, the user moves to a position to mainly browse the display 32 and presses a button associated with the setting of a reference user position or performs a gesture motion. The position specifying circuitry 22 then specifies the user position at this time, and sets a reference user position.

FIG. 3 is a view for explaining a user movement displacement. Assume that the coordinate system is an examination room coordinate system having a display central position O as an origin. In addition, assume that an axis along the long axis of the display 32 is defined as the X-axis, an axis along the short axis of the display 32 is defined as the Y-axis, and an axis which passes through the display central position O and is perpendicular to the display screen of the display 32 is defined as the Z-axis. P0 represents a reference user position, and P1 represents a user position after movement from the reference user position. Assume that the coordinates (x0, y0, z0) of the reference user position P0 are known in advance.

The position specifying circuitry 22 specifies the user position P1 (x1, y1, z1) after movement to specify a user movement displacement. The position specifying circuitry 22 then specifies a user movement displacement based on the coordinates (x0, y0, z0) of the reference user position P0 and the coordinates (x1, y1, z1) of the user position P1 after the movement. In this case, the user movement displacement is the movement angle of the user from the reference user position with respect to the display central position O. The movement angle is defined by a straight line, as one side of the angle, which connects the reference user position P0 and the display central position O, a straight line, as the other side of the angle, which connects the user position P1 to the display central position O, and the display central position O as the vertex of the angle. The movement angle is represented by a component (to be referred to as a horizontal angle hereinafter) θ on the X-Z plane of the movement angle and a component (to be referred to as a vertical angle hereinafter) φ on the Y-Z plane of the movement angle. With the above processing, the position specifying circuitry 22 specifies the user movement displacement based on the reference user position and the user position after the movement.

The above has been the description of the FIG. 3.

A reference user parallax is the parallax of the user who visually recognizes the display 32 at the reference user position. A stereoscopic target position is displayed at the display central position of the display 32. For this reason, the position specifying circuitry 22 specifies a reference user parallax based on the distance from the display central position to the reference user position and the inter-pupil distance (to be referred to as the reference inter-pupil distance hereinafter) of the user at the reference user position. For example, a calculation method such as a trigonometry is used to specify a parallax. The inter-pupil distance is the distance between the pupil position of the right eye and the pupil position of the left eye of the user. Note that the user may input a reference user parallax via the input interface circuitry 20.

The position specifying circuitry 22 includes a device such as a camera for specifying a user movement displacement and a reference user parallax. Note that the device may be another device as long as it can specify a user position and a reference inter-pupil distance. For example, the device may be an infrared sensor, optical sensor, or the like. According to the above description, the user position is the midpoint of a straight line connecting the pupil position of the right eye and the pupil position of the left eye. However, the user position is not limited to the above position as long as the position specifying circuitry 22 can specify how much the face of the user has moved. For example, the user position may be the position of another part of the face, e.g., the position of the mouth or the position of the nose, or the position of a marker attached to the face. Alternatively, one of a set of the light-receiving device and the light-emitting device of an optical sensor may be attached to the user, and the other is attached to the display 32 to make the position specifying circuitry 22 specify a user movement displacement based on an output from the optical sensor.

Note that the control circuitry 30 may store data concerning a reference user position and a reference user parallax in the memory 28 (to be described later), together with accompanying information such as user information and examination information. In addition, according to the above description, a reference user position and a reference user parallax are specified by the position specifying circuitry 22. However, a reference user position is sometimes determined in advance in accordance with the type of procedure. In addition, a reference user position and a reference inter-pupil distance are sometimes determined in accordance with the user who is in charge of a procedure. For this reason, a reference user position and a reference inter-pupil distance may be selected from the user information database stored in the memory 28 (to be described later), as needed, in accordance with a user instruction. The position specifying circuitry 22 performs specifying processing for a user movement displacement in linkage with imaging angle setting processing (to be described later). The position specifying circuitry 22 transmits the specified user movement displacement to the imaging position setting circuitry 23.

The imaging condition setting circuitry 24 includes, for example, a predetermined processor and a memory. The imaging condition setting circuitry 24 sets X-ray imaging conditions based on the X-ray imaging conditions input by the user.

The imaging position setting circuitry 23 includes, for example, a predetermined processor and a memory. The imaging position setting circuitry 23 sets a visual line and an imaging angle set. The imaging position setting circuitry 23 sets an imaging angle set in accordance with the reference visual line input by the user. The imaging angle set includes a left-eye imaging angle and a right-eye imaging angle. A visual line angle corresponding to a visual line direction is represented by the angle formed by the X-axis and the angle formed by the Y-axis, when, for example, a stereoscopic target position is an origin, an axis parallel to the short-axis of the top 14 is the X-axis, an axis along a direction perpendicular to the top 14 surface is the Y-axis, and an axis parallel to the long axis of the top 14 is the Z-axis. In addition, the imaging position setting circuitry 23 re-sets a visual line concerning an object based on a visual line corresponding to the image set currently displayed on the display 32 and a user movement displacement. The imaging position setting circuitry 23 then sets an imaging angle set in accordance with the re-set visual line. Imaging angle set setting processing by the imaging position setting circuitry 23 will be described in detail later. The imaging position setting circuitry 23 transmits the data of the set imaging angle set to the imaging control circuitry 25 and the image selection circuitry 29.

The imaging control circuitry 25 includes, for example, a predetermined processor and a memory. The imaging control circuitry 25 controls each element associated with X-ray imaging. More specifically, the imaging control circuitry 25 controls the high voltage generation circuitry 16 in accordance with the X-ray imaging conditions set by the imaging condition setting circuitry 24. In addition, the imaging control circuitry 25 controls the moving circuitry 19 in accordance with the imaging angle set by the imaging condition setting circuitry 24. At this time, the imaging control circuitry 25 controls the X-ray detector 18 to execute an X-ray imaging operation with the imaging angle set while controlling the high voltage generation circuitry 16 and the moving circuitry 19. The imaging control circuitry 25 then controls the operations of the memory 28, the image generation circuitry 27, the preprocessing circuitry 26, and the like in synchronism with the X-ray imaging operation.

The preprocessing circuitry 26 includes, for example, a predetermined processor and a memory. The preprocessing circuitry 26 executes preprocessing for the electrical signal output from the X-ray detector 18. Preprocessing includes, for example, various types of correction processing, amplification processing, and A/D conversion processing.

The image generation circuitry 27 includes, for example, a predetermined processor and a memory. The image generation circuitry 27 generates X-ray image data based on the preprocessed electrical signal. More specifically, the image generation circuitry 27 generates left-eye image data and right-eye image data (a combination of which will be referred to as an image set hereinafter) respectively corresponding to a left-eye imaging angle and a right-eye imaging angle (imaging angle set). The pixel value assigned to each pixel of an X-ray image is a value or the like corresponding to an X-ray attenuation coefficient concerning a material on an X-ray transmission path.

The memory 28 is a semiconductor storage device such as a Flash SSD (Solid State Disk) as a semiconductor storage element, an HDD (Hard Desk Drive), or the like. The memory 28 stores the data of a plurality of image sets generated by the image generation circuitry 27, together with data concerning the respective corresponding visual line angles and imaging angle sets, under the control of the control circuitry 30. The memory 28 also stores data other than the data concerning the image sets, e.g., X-ray imaging condition data, X-ray imaging angle condition data, inter-pupil distance data, and the data of a user information database. The user information database is a correspondence table associating a plurality of user IDs with a plurality of inter-pupil distances and a plurality of reference user positions. The memory 28 may include a plurality of correspondence tables corresponding to procedure types.

The image selection circuitry 29 includes, for example, a predetermined processor and a memory. The image selection circuitry 29 selects an image set to be displayed on the display 32 (to be described later) from a plurality of image sets stored in the memory 28 (to be described later) based on the imaging angle set set by the imaging position setting circuitry 23. If an image set corresponding to the imaging angle set set by the imaging position setting circuitry 23 is not stored in the memory 28, the image selection circuitry 29 transmits a signal indicating the start of imaging to the imaging control circuitry 25. Note that the ON/OFF status of the processing of selecting an image set from the memory 28 by the image selection circuitry 29 can be changed as needed in accordance with a user instruction.

The control circuitry 30 includes a predetermined processor and a memory. The control circuitry 30 receives the instruction information input via the input interface circuitry 20 and temporarily stores it in the memory. The control circuitry 30 controls each element of the X-ray diagnostic apparatus 1 based on input information.

The display control circuitry 31 includes, for example, a predetermined processor and a memory. The display control circuitry 31 displays, on the display 32 (to be described later), the image set selected by the image selection circuitry 29 so as to allow the user to stereoscopically view at the reference user position.

For example, in a naked-eye type two-parallax lenticular lens scheme, the display control circuitry 31 transmits a video signal obtained by vertically dividing each of a left-eye image and a right-eye image into strips to the display 32. The display 32 displays the left-eye image and the right-eye image divided into strips such that they are alternately arranged. The divided left-eye images and right-eye images are alternately arranged and displayed on the display 32. The display 32 has a lenticular lens on its display surface. A lenticular lens is a lens which changes the position that a visual line reaches depending on the position where the user sees. Adjusting the placement of the lenticular lens allows the right and left eyes to see only the right- and left-eye images, respectively, thereby implementing stereoscopic vision.

In addition, in an eyeglass type frame sequential scheme, the display control circuitry 31 transmits a right-eye image signal to the display 32 after a left-eye image signal in one frame synchronization period. The display 32 displays an image based on the transmitted image signals. The user wearing liquid crystal shutter eyeglasses sees the display 32. The liquid crystal shutters alternately shut the left and right fields of view in synchronism with the display operation of the display 32. The shutters of the eyeglasses open and close perfectly in synchronism with two images to allow the right eye to see only a right-eye image and allow the left eye to see only a left-eye image, thereby implementing stereoscopic vision.

Although the display control circuitry 31 and the display 32 according to this embodiment have been described by taking the two stereoscopic vision schemes as examples, the embodiment can be applied to any stereoscopic vision schemes using parallax. In addition, the embodiment can be applied to any stereoscopic vision schemes which can use multi-parallax techniques.

(Imaging Angle Setting Function)

The imaging angle setting function is a function by which the imaging position setting circuitry 23 of the X-ray diagnostic apparatus 1 according to this embodiment re-sets a visual line concerning an object based on a visual line corresponding to the image set currently displayed on the display 32 and the user movement displacement specified by the position specifying circuitry 22, and automatically sets an imaging angle set corresponding to the re-set visual line. Processing accompanying the imaging angle setting function (to be referred to as imaging angle setting processing hereinafter) will be described with reference to FIG. 4. The imaging angle setting processing is executed under the control of the imaging control circuitry 25.

FIGS. 4A, 4B, 4C, and 4D are views for explaining the imaging angle setting processing performed by the X-ray diagnostic apparatus 1 according to this embodiment.

Figure 4A:
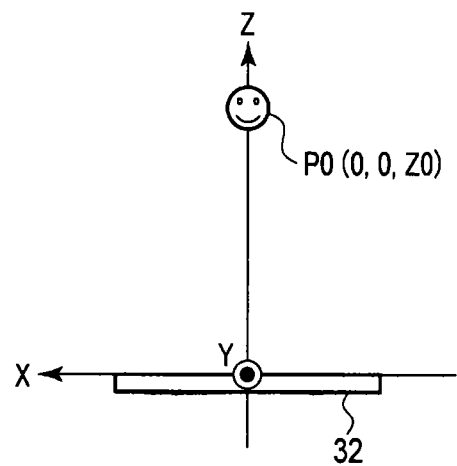
FIG. 4A is a view showing a reference user position in an examination room coordinate system.

FIG. 4A is a view showing a reference user position in an examination room coordinate system.

Figure 4B:
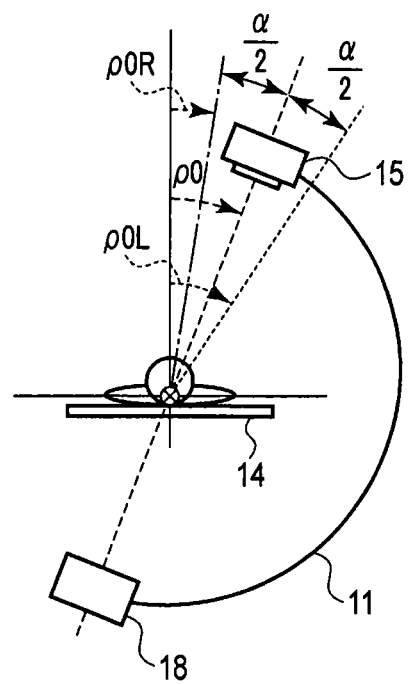
FIG. 4B is a view for explaining an imaging angle set corresponding to the reference user position.

FIG. 4B is a view for explaining an imaging angle set corresponding to a reference user position.

Figure 4C:
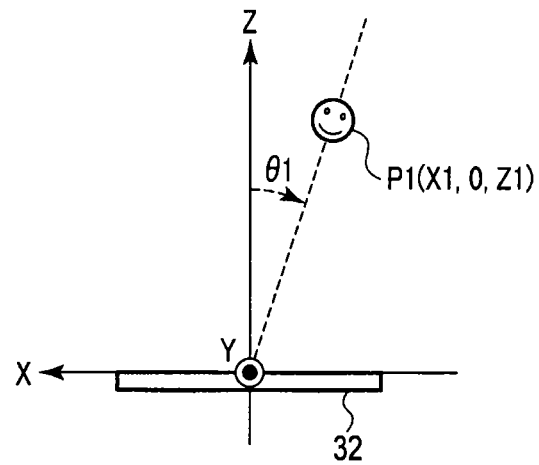
FIG. 4C is a view showing a user position after movement from the reference user position in the examination room coordinate system.

FIG. 4C is a view showing a user position after movement from the reference user position in the examination room coordinate system.

Figure 4D:
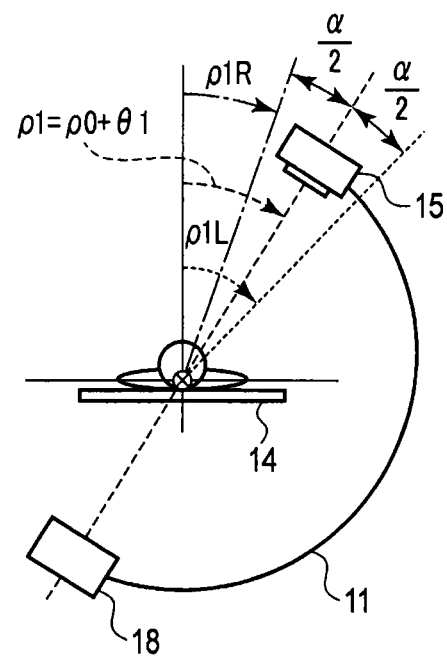
FIG. 4D is a view for explaining an imaging angle set corresponding to a user position after movement.

FIG. 4D is a view for explaining an imaging angle set corresponding to the user position after the movement.

FIGS. 4A and 4C each show an examination room coordinate system having the display central position O as an origin, an axis along the long axis of the display 32 as the X-axis, an axis along the short axis of the display 32 as the Y-axis, and an axis, as the Z-axis, which passes through the display central position O and is perpendicular to the display screen of the display 32.

FIGS. 4B and 4D each show a top coordinate system having a predetermined position on the top 14 as an origin, the Z-axis parallel to the long axis of the top 14, the X-axis parallel to the short axis of the top 14, and the Y-axis perpendicular to the top 14 surface.

Assume that as shown in FIG. 4A, the user is at the reference user position P0 (0, 0, Z0). Assume that a left-eye imaging angle and a right-eye imaging angle (to be referred to as an imaging angle set J0 hereinafter) corresponding to a reference visual line are respectively set to $\rho 0L$ and $\rho 0R$. The imaging position setting circuitry 23 sets the imaging angle set J0 based on a reference visual line and a reference user parallax. More specifically, when a reference visual line is set on a visual line setting image via the input interface circuitry 20, the imaging position setting circuitry 23 specifies a visual line angle $\rho 0$ based on the visual line direction included in the reference visual line. The imaging position setting circuitry 23 then specifies an angle ($\alpha/2$) through which the visual line is tilted from the visual line angle $\rho 0$ to the left-eye imaging angle and an angle ($\alpha/2$) through which the visual line is tilted from the visual line angle $\rho 0$ to the right-eye imaging angle based on a reference user parallax $\alpha$. In addition, the imaging position setting circuitry 23 specifies directions in which the visual line is tilted from the visual line angle $\rho 0$ to the left-eye imaging angle and the right-eye imaging angle based on the display direction included in the reference visual line. Each tilting direction is perpendicular to a straight line indicating a visual line direction and is parallel to a straight line representing the left and right of the display direction. The direction in which the visual line is tilted from a visual line angle to a left-eye imaging angle is opposite to the direction in which the visual line is tilted from a visual line angle to a right-eye imaging angle. With the above processing, the imaging position setting circuitry 23 can set the left-eye imaging angle $\rho 0L$ and the right-eye imaging angle $\rho 0R$ based on the reference visual line and the reference user parallax. Each unit then acquires a left-eye image K0L and a right-eye image K0R (an image set K0) respectively corresponding to the left-eye imaging angle $\rho 0L$ and the right-eye imaging angle $\rho 0R$ (the imaging angle set J0) under the control of the imaging control circuitry 25, and stores the acquired images in the memory 28. The display control circuitry 31 then displays the left-eye image K0L and the right-eye image K0R on the display 32. The user can recognize a stereoscopic vision video concerning the object like that seen when he/she sees a stereoscopic target position from the visual line angle $\rho 0$ by visually recognizing the display 32 from the reference user position P0.

Assume that the user has moved from the reference user position P0 in FIG. 4A to the user position P1 in FIG. 4C. In response to the execution of a specific gesture motion by the user or pressing of the setting switch, the imaging control circuitry 25 executes imaging angle setting processing.

The imaging angle setting processing is executed according to the following procedure. First of all, the position specifying circuitry 22 specifies the user position P1 (X1, 0, Z1) after the movement. For the sake of simplicity, assume that the user has moved in the horizontal direction. The position specifying circuitry 22 then specifies a movement angle $\theta 1$ (user movement displacement) based on the reference user position P0 and the user position P1 after the movement. The movement angle $\theta 1$ includes information concerning a moving direction from the reference user position. The imaging position setting circuitry 23 then specifies a visual line angle $\rho 1$ based on a visual line angle $\rho 0$ corresponding to the image set currently displayed on the display 32 and the movement angle $\theta 1$. The visual line angle $\rho 1$ is the angle obtained by adding the movement angle $\theta 1$ to the visual line angle $\rho 0$. With the above processing, a visual line concerning the object is re-set. The re-set visual line differs in visual line direction from the visual line before it is re-set. The imaging position setting circuitry 23 then specifies an angle ($\alpha/2$) through which the visual line is tilted from the visual line angle $\rho 1$ to the left-eye imaging angle and an angle ($\alpha/2$) through which the visual line is tilted from the visual line angle $\rho 1$ to the right-eye imaging angle based on the reference user parallax. The imaging position setting circuitry 23 specifies directions in which the visual line is tilted from the visual line angle $\rho 1$ to the left-eye imaging angle and the right-eye imaging angle based on the display direction included in the re-set visual line. With the above processing, the imaging position setting circuitry 23 can set a left-eye imaging angle $\rho 1L$ and a right-eye imaging angle $\rho 1R$ (to be referred to as an imaging angle set J1 hereinafter) based on the visual line corresponding to the image set displayed on the display 32 and the reference user parallax. Each unit acquires a left-eye image K1L and a right-eye image K1R (an image set K1) respectively corresponding to the left-eye imaging angle $\rho 1L$ and the right-eye imaging angle $\rho 1R$ (the imaging angle set J1) under the control of the imaging control circuitry 25, and stores the acquired images in the memory 28. The imaging control circuitry 25 automatically executes an acquiring operation for the image set K1 after the imaging angle set J1 is set. The display control circuitry 31 then displays the left-eye image K1L and the right-eye image K1R on the display 32. The user can recognize a stereoscopic vision video like that seen when he/she sees a stereoscopic target position from the visual line angle $\rho 1$ by visually recognizing the display 32 from the reference user position P0.

Note that in this case, triggers for transition to the imaging angle setting processing include a gesture motion by the user and an operation on the input interface circuitry 20. However, other methods may be used. For example, transition to the imaging angle setting processing may be made in response to the detection of a specific word uttered by the user. For this purpose, the X-ray diagnostic apparatus 1 may include, as a constituent element, a sound detection unit including a sound detection device for detecting a specific word uttered by the user.

A series of processing using the X-ray diagnostic apparatus 1 according to this embodiment will be described next with reference to FIG. 5. Assume that the selection processing function of the image selection circuitry 29 is ON.

Figure 5:
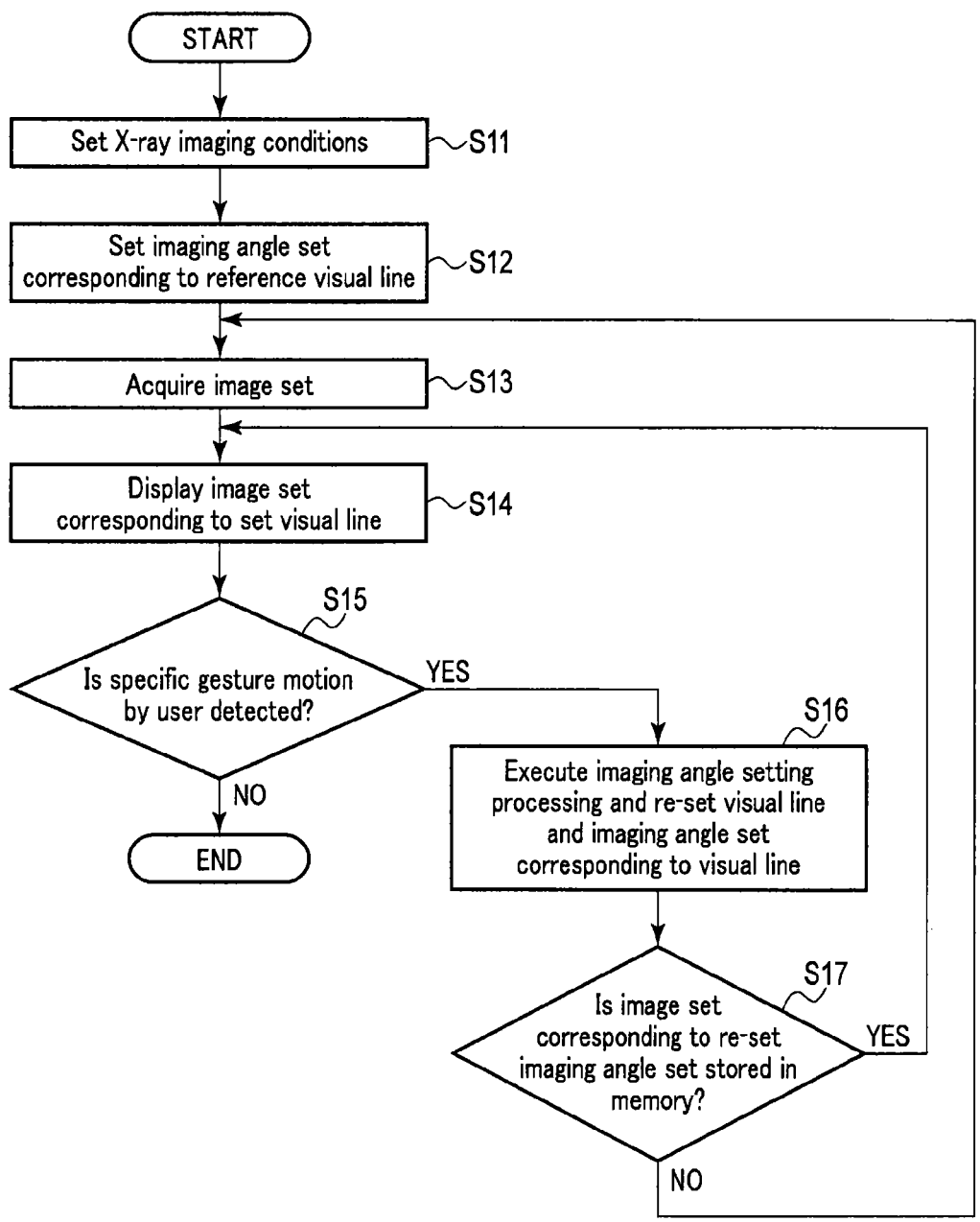
FIG. 5 is a flowchart showing an example of a series of processing operations using the X-ray diagnostic apparatus according to this embodiment.

FIG. 5 is a flowchart showing an example of a series of processing operations using the X-ray diagnostic apparatus 1 according to this embodiment.

(Step S11)

The imaging condition setting circuitry 24 sets X-ray imaging conditions based on the X-ray imaging conditions input by the user via the input interface circuitry 20.

(Step S12)

Based on the reference visual line input by the user via the input interface circuitry 20 and the reference user parallax specified by the position specifying circuitry 22, the imaging position setting circuitry 23 sets an imaging angle set corresponding to the reference visual line.

(Step S13)

When the process shifts from step S12, each unit acquires an image set corresponding to the imaging angle set set by the imaging position setting circuitry 23, under the control of the imaging control circuitry 25, under the X-ray imaging conditions set by the imaging condition setting circuitry 24. The acquired image set data is stored in the memory 28, together with information concerning the reference visual line, information concerning the imaging angle set, and the like.

When the process shifts from step S17, each unit acquires an image set corresponding to the imaging angle set set in step S17 under the control of the imaging control circuitry 25. The acquired image set data is stored in the memory 28, together with information concerning the reference visual line, information concerning the imaging angle set, and the like.

(Step S14)

When the process shifts from step S12 and step S13, the display control circuitry 31 displays, on the display 32, the image set acquired to allow the user, who visually recognizes the display 32 at the reference user position, to obtain stereoscopic vision. The user can recognize a stereoscopic vision video corresponding to the reference visual line by visually recognizing the display 32 from the reference user position.

When the process shifts from step S17 and step S13, the display control circuitry 31 displays, on the display 32, the image set read out to allow the user, who visually recognizes the display 32 at the reference user position, to obtain stereoscopic vision. The user can recognize a stereoscopic vision video like that seen when he/she sees a stereoscopic target position from the visual line angle set in step S16 by visually recognizing the display 32 from the reference user position.

When the process shifts from step S16, the image selection circuitry 29 reads out an image set corresponding to the re-set visual line from the memory 28. The display control circuitry 31 then displays, on the display 32, the image set read out to allow the user, who visually recognizes the display 32 at the reference user position, to obtain stereoscopic vision. The user can recognize a stereoscopic vision video corresponding to the visual line re-set in step S16 by visually recognizing the display 32 from the reference user position.

(Step S15)

The position specifying circuitry 22 executes detection processing for a specific gesture motion by the user. If the position specifying circuitry 22 detects the specific gesture motion by the user, the process shifts to step S16 to execute imaging angle setting processing. If the position specifying circuitry 22 does not detect the specific gesture motion by the user, the series of processing operations by the X-ray diagnostic apparatus 1 is terminated. The shift to the imaging angle setting processing may be made in response to the pressing of the setting switch of the input interface circuitry 20 or the utterance of a specific word by the user.

(Step S16)

The position specifying circuitry 22 and the imaging position setting circuitry 23 execute the imaging angle setting processing. The imaging angle setting processing will re-set a visual line with respect to the object and set an imaging angle set corresponding to the re-set visual line.

(Step S17)

If an image set corresponding to the imaging angle set set in step S16 is stored in the memory 28, the process shifts to step S14. If an image set corresponding to the imaging angle set set in step S16 is not stored in the memory 28, the process shifts to step S13.

It is possible to repeatedly execute the imaging angle setting processing by the X-ray diagnostic apparatus 1 in response to the execution of the specific gesture motion by the user. Note that when a visual line is re-set while the image set selection processing by the image generation unit 29 is OFF, the X-ray diagnostic apparatus 1 always acquires an image set corresponding to the re-set visual line. This allows the user to recognize a stereoscopic vision video corresponding to another visual line in real time.

According to the imaging angle setting function described above, the following effects can be obtained.

The X-ray diagnostic apparatus 1 can set a reference visual line in accordance with a user instruction on the visual line setting image displayed on the display 32. The user can recognize a stereoscopic vision video corresponding to the reference visual line concerning the object by visually recognizing the display 32 at the reference user position. This stereoscopic vision video is a video like that seen when the user sees a stereoscopic target position from the visual line direction corresponding to the reference visual line, and is centered on the stereoscopic target position corresponding to the reference visual line. In addition, the top, bottom, left, and right of the stereoscopic vision video correspond to a display direction corresponding to the reference visual line.

With the imaging angle setting function, the user can recognize a stereoscopic vision video obtained by rotating a recognized stereoscopic vision video by only moving the position of the face from the reference user position. At this time, the top, bottom, left, and right directions of the stereoscopic vision video are the same as those of the stereoscopic vision video before the rotation.

In this series of processing operations, the X-ray diagnostic apparatus 1 executes the following processing. The X-ray diagnostic apparatus 1 specifies a user movement displacement from a reference user position to a user position after movement. The X-ray diagnostic apparatus 1 re-sets a visual line corresponding to the user position after the movement based on the user movement displacement and the visual line corresponding to the image set currently displayed on the display 32. The X-ray diagnostic apparatus 1 sets an imaging angle set (a left-eye imaging angle and a right-eye imaging angle) corresponding to the re-set visual line based on the re-set visual line. The X-ray diagnostic apparatus 1 then acquires an image set (a left-eye image and a right-eye image) corresponding to the imaging angle set (the left-eye imaging angle and the right-eye imaging angle), and displays the image set on the display 32. The user can recognize a stereoscopic vision video corresponding to the re-set visual line by visually recognizing the display 32 at the reference user position. The stereoscopic vision video corresponding to the re-set visual line is a stereoscopic vision video concerning the object like that seen when the user sees the stereoscopic target position from the user position after the movement. That is, when wanting to see a recognized stereoscopic vision video from a different direction, the user can recognize the stereoscopic vision video like that seen from the position after the movement by only moving the face in the direction in which he/she wants to see the video. The user can recognize a stereoscopic vision video concerning an object when seeing a stereoscopic target position from a plurality of directions by an intuitive motion of moving the face. This can therefore improve the efficiency of a surgical operation and the like by the user. In addition, the X-ray diagnostic apparatus 1 acquires only an image set corresponding to a re-set visual line instead of acquiring a plurality of image sets corresponding to a plurality of visual lines in advance. Therefore, the X-ray diagnostic apparatus 1 can also suppress an exposure dose. That is, the X-ray diagnostic apparatus 1 including the imaging angle setting function can improve operability while suppressing an exposure dose in diagnosis, medical treatment, or the like using the stereoscopic vision technique.

In addition, if an image set corresponding to a re-set visual line is stored in the memory 28, the image selection circuitry 29 selects the image set corresponding to the re-set visual line from the memory 28, and displays the image set on the display 32. This therefore allows the user to recognize a stereoscopic vision video corresponding to the re-set visual line without newly performing imaging. The X-ray diagnostic apparatus 1 can therefore suppress an exposure dose.

Note that referring to FIG. 5, imaging angle setting processing is executed in response to the detection of a specific gesture motion by the user, the detection of the utterance of a specific word by the user, or the pressing of the setting switch of the input interface circuitry 20, that is, in accordance with a user instruction. However, the imaging angle setting processing may be automatically repeated under the control of the imaging control circuitry 25. In this case, the imaging control circuitry 25 executes imaging angle setting processing at predetermined time intervals. The predetermined time interval is set in advance by the user and can be changed as needed in accordance with a user instruction. It is possible to change, in accordance with a user instruction, whether imaging angle setting processing is automatically executed or executed in accordance with a user instruction. Since imaging angle setting processing can be automatically executed, the user need not perform any specific gesture motion, utter a specific word, or operate the input interface circuitry 20, the operability can be improved as compared with the case in which imaging angle setting processing is manually performed. In this case, when a user movement displacement is smaller than a preset threshold, the imaging control circuitry 25 may be inhibited from executing imaging angle setting processing. This makes it possible to avoid the execution of imaging angle setting processing which is not intended by the user.

In addition, referring to FIG. 4, the visual line angle $\rho1$ corresponding to the visual line after the movement is the angle obtained by adding the movement angle $\theta1$ to the visual line angle $\rho0$ corresponding to the visual line before the movement. This allows the user to recognize a stereoscopic vision video like that seen when he/she sees a stereoscopic target position from the position after the movement by only moving the face from the reference position. That is, since a movement angle from a reference position with respect to the display central position one-to-one corresponds to the difference between visual line angles before and after the movement, the user can intuitively change the visual line with respect to the object. However, when wanting to see a currently recognized stereoscopic vision video rotated 70°, the user needs to move his/her face 70° around the reference position in the horizontal direction with respect to the display central position. It is sometimes difficult for the user to move largely from the reference position during a procedure. For this reason, the visual line angle $\rho1$ may be the angle obtained by adding the visual line angle $\rho0$ to the angle obtained by multiplying the movement angle $\theta1$ by a coefficient $\beta$ set in advance by the user. This makes it possible to re-set a visual line in the same manner as when the face of the user moves largely even when the face of the user actually moves little. That is, even the user who is performing a procedure in a limited movable range can recognize a stereoscopic vision video concerning an object from various directions.

In addition, in this embodiment, a user movement displacement is regarded as the movement angle of the user from a reference user position with respect to the display central position O. That is, a user movement displacement is specified in accordance with the moving motion of the face of the user. However, the user sometimes cannot move from a reference position during a procedure. For this reason, a user movement displacement may not be based on the moving motion of the face of the user. For example, a user movement displacement may be the motion of tilting the face of the user, the motion of changing the direction of the face of the user, or the like.

If a user movement displacement is based on the motion of tilting the face of the user, the position specifying circuitry 22 specifies the tilt angle and direction of the face of the user from a reference user position. More specifically, the position specifying circuitry 22 specifies the pupil position of the left eye and the pupil position of the right eye of the user. The position specifying circuitry 22 then specifies an angle (to be referred to as a tilt angle hereinafter) defined by a line connecting the pupil of the left eye and the pupil of the right eye when the user is at a reference user position and the same line after the user tilts his/her face. The imaging position setting circuitry 23 then re-sets a visual line based on a visual line corresponding to the currently displayed stereoscopic vision video and the tilt angle. A method of re-setting a visual line in accordance with a tilt angle is set in advance by the user. For example, when the tilt angle is 10° on the right, the imaging position setting circuitry 23 re-sets the visual line corresponding to the currently displayed stereoscopic vision video to the visual line rotated through 10° rightward in the horizontal direction.

When a user movement displacement is based on the motion of changing the direction of the face of the user, the position specifying circuitry 22 specifies the direction of the face of the user and the speed of changing the direction of the face based on the moving direction of a feature point on the face and a movement distance of the feature point per unit time. The imaging position setting circuitry 23 re-sets a visual line based on the visual line corresponding to the currently displayed stereoscopic vision video, the direction of the face, and the speed of changing the direction of the face. More specifically, for example, the imaging position setting circuitry 23 decides a direction in which the visual line is changed, based on the visual line direction and the direction of the face. The imaging position setting circuitry 23 then decides an angle at which the visual line is changed, based on the speed of changing the direction of the face.

The imaging position setting circuitry 23 re-sets an imaging angle set corresponding to the re-set visual line. An image set corresponding to the re-set imaging angle set is acquired and displayed on the display 32 under the control of the imaging control circuitry 25. The user can recognize a stereoscopic vision video corresponding to the re-set visual line by visually recognizing the display 32 at the reference user position. With the above processing, the imaging position setting circuitry 23 re-sets a visual line based on the motion of tilting the face of the user or the motion of changing the direction of the face of the user.

(First Modification)

The X-ray diagnostic apparatus 1 according to the first modification will be described.

The X-ray diagnostic apparatus 1 according to this embodiment is based on the premise that the user visually recognizes the display 32 at a reference user position. This is because when the user frequently performs operations at a predetermined position (reference user position), the user visually recognizes the display 32 at almost a fixed position. However, the user sometimes wishes to see a currently recognized stereoscopic vision video by rotating it in a specific direction for a little while. When using the X-ray diagnostic apparatus 1, the user can rotate the stereoscopic vision video by moving the video from the reference user position in a specific direction. The user can recognize the stereoscopic vision video after the rotation by visually recognizing the display 32 at the reference user position. When, however, returning the stereoscopic vision video after the rotation to the stereoscopic vision video before the rotation, the user needs to move his/her face from the reference user position in a direction opposite to the specific direction described above. This is because the rotation of the stereoscopic vision video is performed in accordance with a user movement displacement from the reference user position. When wanting to return a stereoscopic vision video to the original stereoscopic vision video after seeing it for a little while upon rotating the stereoscopic vision video in a specific direction, the user needs to reciprocate twice with the reference user position being a starting point. If the user needs to reciprocate twice even when wanting to see a stereoscopic vision video for a little while upon rotting it in a different direction, the operability may deteriorate.

The X-ray diagnostic apparatus 1 according to the first modification aims at solving the above problem. The X-ray diagnostic apparatus 1 according to the first modification can change the reference user position. That is, the user can recognize, at the user position after movement, a stereoscopic vision video like that seen when he/she sees a stereoscopic target position from the user position after the movement. When wanting to return the stereoscopic vision video to the stereoscopic vision video before the movement, the user is only required to return his/her face to the user position before the movement. This makes it possible to see a stereoscopic vision video from a different direction only for a little while by only reciprocating the face once. Therefore, in addition to the effects of the X-ray diagnostic apparatus 1 according to this embodiment, the X-ray diagnostic apparatus 1 according to the first modification can improve operability when the user wants to see a stereoscopic vision video from a different direction for a little while.

Note that whether a reference user position is allowed to be changed can be changed as needed in accordance with the user instruction issued via the input interface circuitry 20. This change instruction may be switched in accordance with a gesture motion by the user and the utterance of a specific word.

(Second Modification)

The X-ray diagnostic apparatus 1 according to the second modification will be described.

With the X-ray diagnostic apparatus 1 according to this embodiment, when the user wants to see a recognized stereoscopic vision video from a different direction, he/she can recognize a stereoscopic vision video like that seen from the position after the movement, by only moving his/her face in the direction in which he/she wants to see. In this case, the top, bottom, left, and right of the stereoscopic vision video after a visual line is re-set are the same as those of the stereoscopic vision video before the visual line is re-set. Therefore, the upper, lower, left, and right directions of the stereoscopic vision video recognized by the user always remain the same. However, the user sometimes wants to see a recognized stereoscopic vision video while tilting it (wants to change the top, bottom, left, and right of the video). When, for example, wanting to make the traveling direction of a catheter during a catheter procedure correspond to the top and bottom of a video, he/she sometimes wants to tilt the currently recognized stereoscopic vision video in accordance with the traveling direction of the catheter while maintaining the visual line direction. Using the X-ray diagnostic apparatus 1 according to this embodiment will cope with the re-setting of a visual line direction of a visual line. However, the apparatus does not cope with the re-setting of a display direction.

The X-ray diagnostic apparatus 1 according to the second modification aims at solving the above problem. More specifically, the X-ray diagnostic apparatus 1 according to the second modification can re-set a display direction in accordance with the tilt angle of the face of the user. Since a display direction can be re-set, a recognized stereoscopic vision video can be tilted in accordance with the tilt angle of the face of the user.

The position specifying circuitry 22 specifies the tilt angle of the face of the user from a reference user position. More specifically, the position specifying circuitry 22 specifies the pupil position of the left eye and the pupil position of the right eye of the user. The position specifying circuitry 22 then specifies an angle (to be referred to as a tilt angle hereinafter) defined by a line connecting the pupil of the left eye and the pupil of the right eye when the user is at a reference user position and the same line after the user tilts his/her face. The imaging position setting circuitry 23 re-sets a visual line based on a visual line corresponding to the image set currently displayed on the display 32 and the tilt angle. More specifically, the imaging position setting circuitry 23 re-sets a display direction in accordance with the tilt angle. The imaging position setting circuitry 23 then re-sets an imaging angle set based on the re-set visual line and a reference user parallax. An image set corresponding to the re-set imaging angle set is acquired and displayed on the display 32 under the control of the imaging control circuitry 25. The user can recognize a stereoscopic vision video corresponding to the re-set visual line by visually recognizing the display 32 at the reference user position. The stereoscopic vision video corresponding to the re-set visual line is the video obtained by tilting the stereoscopic vision video corresponding to the visual line before re-setting. The tilt direction corresponds to the direction in which the user tilts his/her face. In addition to the effects of the X-ray diagnostic apparatus 1 according to this embodiment, the X-ray diagnostic apparatus 1 according to the second modification can improve operability when the user wants to recognize a stereoscopic vision video upon tilting it.

(Third Modification)

The X-ray diagnostic apparatus 1 according to the third modification will be described.

In the X-ray diagnostic apparatus 1 according to this embodiment, the X-ray diagnostic apparatus 1 according to the first modification, and the X-ray diagnostic apparatus 1 according to the second modification, a re-set visual line depends on a user movement displacement. However, in diagnosis, medical treatment, and the like of an object, a visual line direction in which the user needs to see the object, a display direction, and the like are sometimes determined in advance in accordance with the type of region, the type of procedure, or the like. In the use of the X-ray diagnostic apparatus 1 according to this embodiment, the user needs to give consideration to the moving direction of the face and the movement amount of the face when he/she wants to change the visual line corresponding to the currently displayed stereoscopic vision video to a predetermined visual line. If the movement amount is large, the user cannot recognize a stereoscopic vision video in the predetermined direction. For this reason, in order to obtain a stereoscopic vision video corresponding to the predetermined visual line, the user sometimes needs to repeatedly move his/her face. However, when the user needs to repeatedly move his/her face, the operability of the user may deteriorate.

The X-ray diagnostic apparatus 1 according to the third modification aims at solving the above problem. The user of the X-ray diagnostic apparatus 1 according to the second modification can set a plurality of visual lines by operating a visual line setting image via the input interface circuitry 20. Methods of setting a plurality of visual lines on a visual line setting image include a method of manually setting visual lines and a method of semi-automatically setting visual lines.

In the method of totally manually setting visual lines, a plurality of visual lines are set one by one in accordance with a user instruction. The method of setting a visual line in accordance with a user instruction is the same as the method of setting a reference visual line in the X-ray diagnostic apparatus 1 according to this embodiment.

In the method of semi-automatically setting visual lines, a reference visual line of a plurality of visual lines is set in accordance with a user instruction. Other visual lines are set in accordance with the reference visual line and a preset method. In the method of semi-automatically setting visual lines, when, for example, a reference visual line is set by the user, a plurality of visual lines are set at predetermined angular intervals along the upper and lower directions of the visual line setting image at the time of the setting of the reference visual line. In addition, when, for example, a reference visual line is set by the user, a plurality of visual lines are set at predetermined angular intervals along the upper and lower directions of the visual line setting image at the time of the setting of the reference visual line. Furthermore, the above two methods may be combined.

The position specifying circuitry 22 specifies a visual line switching motion by the user. A visual line switching motion is a motion for switching a visual line corresponding to the image set displayed on the display 32 to another preset visual line. Therefore, after the visual line switching motion, the display 32 displays an image set corresponding to another visual line. The user can recognize a stereoscopic vision video corresponding to another visual line by visually recognizing the display 32 at the reference user position. A visual line switching motion by the user includes, for example, moving the face of the user and making a gesture. Note that a visual line switching motion can also be replaced with the utterance of a specific word by the user. The position specifying circuitry 22 specifies a user movement displacement. In addition, the position specifying circuitry 22 specifies a gesture motion by the user. A gesture motion includes, for example, hand waving and finger pointing. A visual line switching motion can be set in accordance with a user instruction via the input interface circuitry 20. Modes of specifying a visual line switching motion by the position specifying circuitry 22 include a continuous mode and a manual mode. These modes can be changed as needed in accordance with a user instruction.

In the continuous mode, the position specifying circuitry 22 specifies whether the user has executed a visual line switching motion. The time intervals at which such a motion is specified can be changed as needed in accordance with a user instruction. In order to prevent the occurrence of visual line switching which is not intended by the user, a visual line switching motion is preferably a motion which the user does not usually perform and does not place much load on the user during a procedure. In addition, in order to clarify whether a given motion is a visual line switching motion, the position specifying circuitry 22 may specify a visual line switching motion in accordance with the speed of a gesture motion, the magnitude of the motion, and the duration time of the motion.

In the manual mode, the position specifying circuitry 22 starts specifying a visual line switching motion in response to pressing of a switch (to be referred to as a shift switch hereinafter) for a shift to the mode of specifying a visual line switching motion using the position specifying circuitry 22. According to the above description, the shift switch serves as a trigger for a shift. However, a shift to the mode of specifying a visual line switching motion using the position specifying circuitry 22 may be triggered by the utterance of a specific word by the user or the detection of a gesture motion. The user executes a visual line switching motion upon pressing the shift switch.

Figure 6:
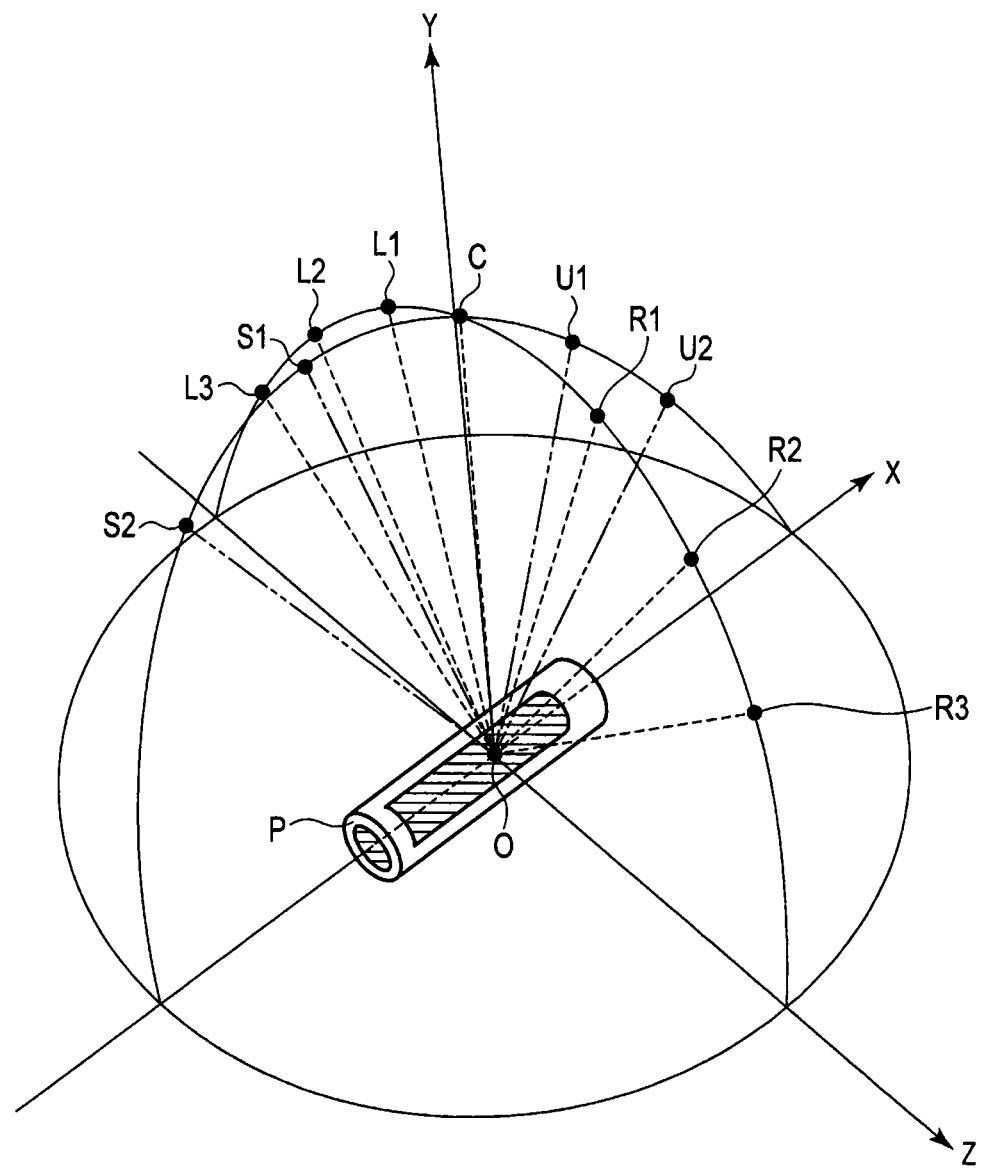
FIG. 6 is a view showing a plurality of visual lines set with respect to a stereoscopic target position.
Figure 7:
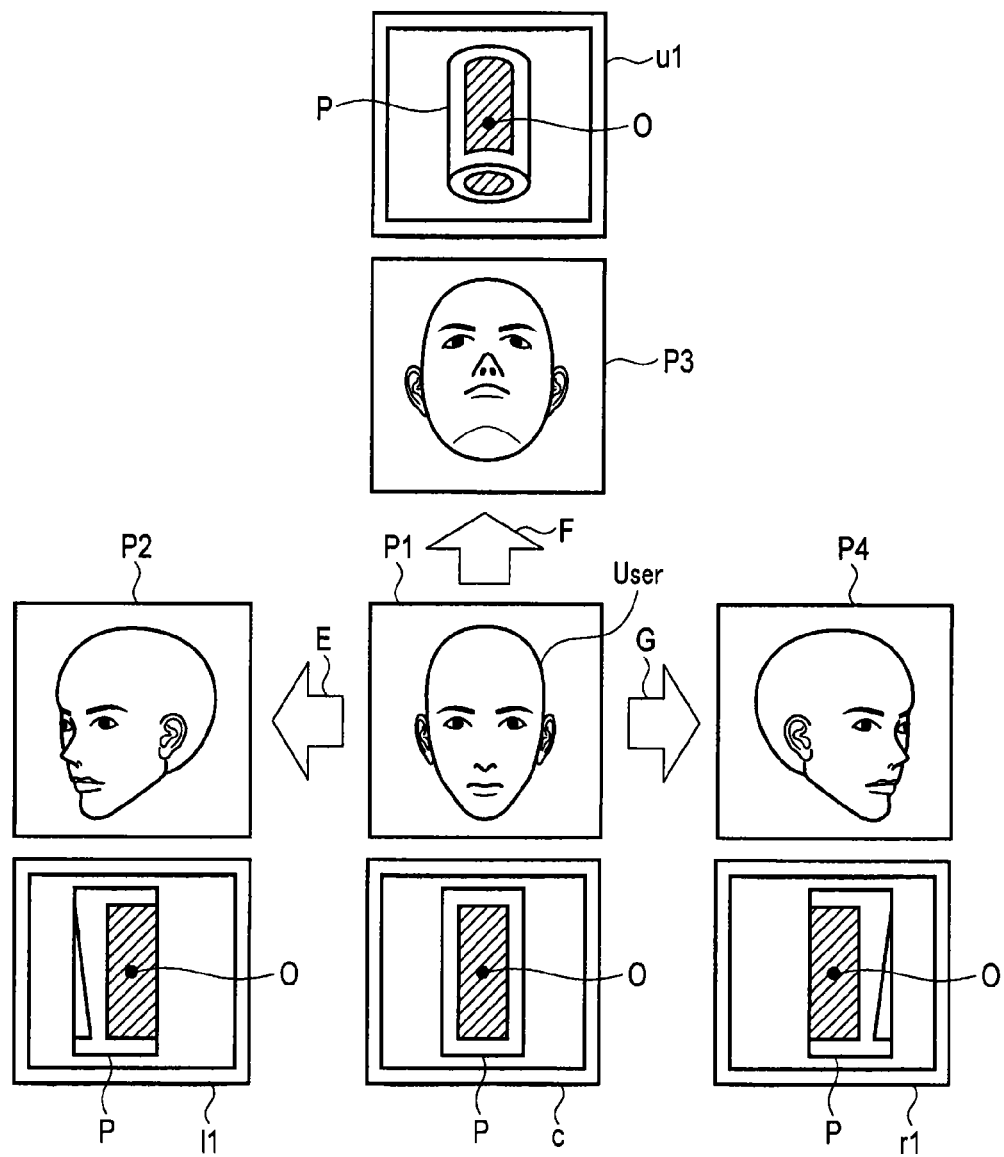
FIG. 7 is a view showing screen transition on a display unit at the time of a visual line switching motion in correspondence with FIG. 6.

FIGS. 6 and 7 are views for explaining a visual line switching motion in the X-ray diagnostic apparatus 1 according to the third modification.

FIG. 6 is a view showing a plurality of visual lines set with respect to a stereoscopic target position.

FIG. 7 is a view corresponding to FIG. 6 and showing the screen transition of the display 32 at the time of a visual line switching motion.

The visual line switching motion performed by the user and the image displayed on the display 32 after the visual line switching motion will be described below with reference to FIGS. 6 and 7.

Referring to FIG. 6, reference symbol P denotes a cylindrical tube imitating an object; O, a stereoscopic target position; and C, the visual line direction of a reference visual line with respect to the stereoscopic target position. With regard to a display direction, the upper, lower, right, and left directions of an image respectively correspond to the +X direction, −X direction, +Z direction, and −Z direction. Reference symbols L1 to L3, R1 to R3, U1 and U2, and S1 and S2 respectively denote a plurality of visual lines corresponding to the stereoscopic target position.

Referring to FIG. 7, reference symbols P1 to P4 denote images of the user imaged by the camera of the position specifying circuitry 22. The image P1 is an image of the user who visually recognizes the display 32 at the reference user position. The images P2, P3, and P4 are respectively images of the user after he/she has performed visual line switching motions E, F, and G. The visual line switching motions E, F, and G are respectively the motions of the user, more specifically, facing right, left, and up. Assume that an image set corresponding to the reference visual line C is currently displayed on the display 32. The user therefore recognizes a stereoscopic vision video c corresponding to the reference visual line C by visually recognizing the display 32 at the reference user position. The stereoscopic vision video c is a stereoscopic vision video concerning the object P like that seen when the user sees the stereoscopic target position O from a visual line direction corresponding to the reference visual line C. When the position specifying circuitry 22 specifies the visual line switching motion E, the imaging position setting circuitry 23 changes the visual line from the reference visual line C to the visual line L1. The visual line switching motion E is a motion in which the user faces right. This motion means that the user wants to rotate the stereoscopic vision video c rightward, i.e., the user wants to see the stereoscopic target position O from the left direction. Therefore, the visual line is changed from the reference visual line C to the visual line L1. The data of an image set corresponding to the visual line L1 is read out from the memory 28 under the control of the imaging control circuitry 25. If the data of the image set corresponding to the visual line L1 is not stored in the memory 28, the data of the image set corresponding to the visual line L1 is acquired by each unit under the control of the imaging control circuitry 25. The image set corresponding to the visual line L1 is displayed on the display 32. The user can recognize a stereoscopic vision video l1 corresponding to the visual line L1 by visually recognizing the display 32 at the reference user position. The stereoscopic vision video l1 is a stereoscopic vision video of the object like that seen when the user sees the stereoscopic target position O from the direction of the visual line L1.

Assume that the visual line switching motion F is specified instead of the above visual line switching motion E. The visual line switching motion F is a motion in which the user faces upward. This motion means that the user wants to rotate the stereoscopic vision video c upward, i.e., the user wants to see the stereoscopic target position O from the down direction. Therefore, the visual line is changed from the reference visual line C to the visual line S1. The user can recognize a stereoscopic vision video s1 corresponding to the visual line S1.

Assume that the visual line switching motion G is specified instead of the above visual line switching motion E. The visual line switching motion G is a motion in which the user faces left. This motion means that the user wants to rotate the stereoscopic vision video c leftward, i.e., the user wants to see the stereoscopic target position O from the right direction. Therefore, the visual line is changed from the reference visual line C to the visual line R1. The user can recognize a stereoscopic vision video r1 of the object like that seen when he/she sees the stereoscopic target position O from the direction of the visual line R1.

In addition, when the position specifying circuitry 22 specifies the visual line switching motion E after the visual line switching motion E described above is specified, the imaging position setting circuitry 23 changes the visual line from the visual line L1 to the visual line L2. The user can recognize a stereoscopic vision video corresponding to the visual line L2.

Note that the imaging position setting circuitry 23 changes the visual line from the reference visual line to the visual line L1 in accordance with the visual line switching motion E. However, the imaging position setting circuitry 23 may change the visual line from the reference visual line to the visual line L2 or L3 in accordance with the magnitude, speed, and duration time of the visual line switching motion.

That is, the imaging position setting circuitry 23 may decide a visual line switching direction in accordance with the type of visual line switching motion, and decide a visual line switching amount in accordance with at least one of the magnitude, speed, and duration time of the visual line switching motion.

In the above visual line switching processing, when the user faces right, the stereoscopic vision video is rotated rightward. That is, the moving direction of the user position corresponds to the visual line switching direction. This allows the user to intuitively switch the visual line. However, the moving direction of the user position need not correspond to the visual line switching direction. The X-ray diagnostic apparatus 1 according to the third modification having the above switching processing function can switch the visual line corresponding to a currently displayed image set to another visual line. Another visual line is one of a plurality of visual lines set in advance by the user. The X-ray diagnostic apparatus 1 according to the third modification specifies another visual line described above from a plurality of visual lines set in advance by the user in accordance with the visual line corresponding to a currently displayed image set and a specified visual line switching motion. The user can recognize a stereoscopic vision video corresponding to another visual line. When a stereoscopic target position where it is necessary to see an object, a visual line direction, and a display direction are determined in advance, the user can re-set a visual line corresponding to a recognized stereoscopic vision video to one of a plurality of preset visual lines by only moving the face. A plurality of image sets corresponding to a plurality of visual lines are not acquired in advance, but an image set corresponding to a visual line re-set in accordance with a user movement displacement is acquired each time. In addition, if an image set corresponding to a re-set visual line has already been acquired, setting can be made to avoid re-acquisition. Therefore, the X-ray diagnostic apparatus 1 according to the third modification can improve operability while suppressing an exposure dose in diagnosis, medical treatment, or the like for an object.

Some embodiments of the present invention have been described above. However, these embodiments are presented merely as examples and are not intended to restrict the scope of the invention. These embodiments can be carried out in various other forms, and various omissions, replacements, and alterations can be made without departing from the spirit of the invention.

For example, this embodiment describes that a visual line direction concerning a visual line concerning an object, can be re-set in accordance with a user movement displacement but does not describe that a display direction can be re-set. In contrast to this, the second modification does not describe that a visual line direction concerning a visual line concerning an object, can be re-set in accordance with a user movement displacement but describes that a display direction can be re-set. However, the function of the second modification may be added to the embodiment. This enables the X-ray diagnostic apparatus 1 to re-set a visual line direction and a display direction concerning a visual line concerning an object, in accordance with a user movement displacement.

In addition, an object of the present invention is to improve operability while suppressing an exposure dose in diagnosis, medical treatment, or the like for an object. This embodiment has exemplified stereoscopic vision. However, the present invention aims at re-setting an imaging position in accordance with the position of the face of the user or the movement displacement of the face and acquiring an X-ray image corresponding to the re-set imaging position. Therefore, the scope of the present invention is not limited to stereoscopic vision.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
an X-ray tube configured to generate X-rays;
an X-ray detector configured to detect X-rays generated from the X-ray tube and transmitted through an object;
a supporting mechanism configured to support the X-ray tube and the X-ray detector in directions to face each other;
a display configured to display an X-ray image concerning the object based on an output from the X-ray detector;
processing circuitry configured to:
specify a movement displacement of a user who is visually recognizing the display, based on positions of a face of the user before and after movement; and
move the supporting mechanism to a left-eye imaging position and a right-eye imaging position corresponding to the specified movement displacement of the user.

2. The X-ray diagnostic apparatus of claim 1, wherein the processing circuitry is further configured to specify a movement displacement of the user based on a reference position and the position of the face of the user after movement.

3. The X-ray diagnostic apparatus of claim 2, wherein the processing circuity is further configured to specify the movement displacement based on an angle through which and a direction in which the face of the user tilts from the reference position or based on a moving speed of the face of the user and a direction of the face of the user.

4. The X-ray diagnostic apparatus of claim 1, wherein the processing circuitry is further configured to:
input a plurality of left-eye imaging position candidates and a plurality of right-eye imaging position candidates with respect to the object, and
move the supporting mechanism to one left-eye imaging position candidate and one right-eye imaging position candidate selected from the plurality of left-eye imaging position candidates and the plurality of right-eye imaging position candidates based on the movement displacement of the user to change the imaging position.

5. The X-ray diagnostic apparatus of claim 1, wherein the processing circuitry is further configured to:
input a visual line concerning the object;
set the left-eye imaging position and the right-eye imaging position which correspond to the visual line based on the visual line and a parallax;
re-set the visual line based on a movement displacement of the user;
re-set the left-eye imaging position and the right-eye imaging position which correspond to the re-set visual line; and
move the supporting mechanism to the set left-eye imaging position and the set right-eye imaging position.

6. The X-ray diagnostic apparatus of claim 1, wherein the processing circuitry is further configured to:
set an imaging position of the object in accordance with an instruction from the user;
set an imaging position corresponding to the position of the face after movement of the user based on an imaging position corresponding to the position of the face of the user before movement and a movement displacement of the user; and
move the supporting mechanism to the left-eye imaging position and the right-eye imaging position corresponding to the position of the face of the user after movement.

7. The X-ray diagnostic apparatus of claim 6, wherein the processing circuitry is further configured to set an imaging position corresponding to the position of the face after movement of the user based on a value obtained by multiplying a parameter representing a movement amount of the face of the user, which is included in a movement displacement of the user, by a predetermined coefficient, a moving direction of the user included in the movement displacement of the user, and an imaging position corresponding to the position of the face before the movement of the user.

8. The X-ray diagnostic apparatus of claim 1, wherein the processing circuitry is further configured to move the supporting mechanism to the left-eye imaging position and the right-eye imaging position corresponding to the specified movement displacement of the user when a movement amount of the face of the user included in the movement displacement of the user is larger than a predetermined value.

9. The X-ray diagnostic apparatus of claim 1, wherein the processing circuitry is further configured to move the supporting mechanism in accordance with the specified position of the face of the user in response to detection of a specific gesture motion of the user or detection of utterance of a specific word by the user.

10. The X-ray diagnostic apparatus of claim 5, wherein the display displays a left-eye image and a right-eye image respectively corresponding to the re-set left-eye imaging position and the re-set right-eye imaging position so as to enable stereoscopic vision at a position before the movement of the user or a position after the movement of the user.

* * * * *